United States Patent
Kovi et al.

(10) Patent No.: US 11,447,499 B2
(45) Date of Patent: Sep. 20, 2022

(54) PROCESS FOR THE PREPARATION OF ERIBULIN MESYLATE INTERMEDIATE

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Shivnath Sahebrao Patil, Dhule (IN)

(73) Assignee: RK PHARMA INC., Pearl River, NY (US)

( * ) Notice: Subject to any disclaimer, the term of this patent is extended or adjusted under 35 U.S.C. 154(b) by 0 days.

(21) Appl. No.: 16/898,794

(22) Filed: Jun. 11, 2020

(65) Prior Publication Data
US 2021/0040107 A1 Feb. 11, 2021

(30) Foreign Application Priority Data
Jun. 14, 2019 (IN) .............................. 201921023560

(51) Int. Cl.
*C07D 493/22* (2006.01)

(52) U.S. Cl.
CPC .................................. *C07D 493/22* (2013.01)

(58) Field of Classification Search
CPC .................................................... C07D 493/22
USPC .......................................................... 549/228
See application file for complete search history.

(56) References Cited

U.S. PATENT DOCUMENTS

| 6,214,865 | B1 | 4/2001 | Littlefield et al. |
| 9,303,039 | B2 | 4/2016 | Zhang et al. |
| 9,783,549 | B2 * | 10/2017 | Fang .................... C07D 407/14 |
| 2018/0009825 | A1 * | 1/2018 | Kovi .................... C07F 7/1804 |

FOREIGN PATENT DOCUMENTS

| WO | 2005118565 A1 | 12/2005 |
| WO | 2009046308 | 4/2009 |
| WO | 2009064029 A1 | 5/2009 |
| WO | 2009124237 A1 | 10/2009 |

OTHER PUBLICATIONS

Wanjun Zheng et al Macrocyclic ketone analogues of halichondrin B (Year: 2004).*
Aicher, T. D. et al., J. Am. Chem. Soc. 114:3162-3164 (1992).
Austad et al., Synlett 24(3):333-337 (2013).
Austad et al., Synlett. 24(3):327-332 (2013).
Chase et al., Synlett 24(3):323-326 (2013).

* cited by examiner

*Primary Examiner* — Timothy R Rozof
(74) *Attorney, Agent, or Firm* — Antonio Papageorgiou

(57) ABSTRACT

The present application provides improved processes for the synthesis of eribulin intermediate, which generally comprise the steps of: a) De-protecting the eribulin-enone (compound 1) in tetrahydrofuran by using TBAF solution, buffered with imidazole HCl in the presence of molecular sieve and sodium sulphate to get an insitu mixture of eribulin-dione diastereomer at C12 carbon (compound 2). Then ketalization may be performed of eribulin-dione insitu intermediate containing mixture of diastereomer at C12 carbon (compound 2) with PPTS in dichloromethane to yield eribulin-diol (compound 3).

1 Claim, 1 Drawing Sheet

PROCESS FOR THE PREPARATION OF ERIBULIN MESYLATE INTERMEDIATE

FIELD OF THE INVENTION

The present application relates to intermediate preparations of eribulin mesylate (compound 6). More specifically, the present application relates to improved processes for the preparation of the eribulin mesylate intermediate eribulin-dione (compound 2).

BACKGROUND

Halichondrin B is a potent anticancer agent originally isolated from the marine sponge *Halichondria okadai*, and subsequently found in *Axinella* sp., *Phakellia carteri*, and *Lissodendoryx* sp. A total synthesis of halichondrin B was published in 1992 (Aicher, T. D. et al., J. Am. Chem. Soc. 114:3162-3164).

Eribulin mesylate (also called Halaven®, E7389, and the mesylate salt of B1939), a nontaxane microtubule dynamics inhibitor, is a structurally simplified, synthetic analogue of halichondrin B. The chemical name for eribulin mesylate is 11,15:18,21:24,28Triepoxy-7,9-ethano-12,15-methano-9H,15H-furo[3,2-i]furo[2',3':5,6]pyrano[4,3-b][1,4]dioxacyclopentacosin-5(4H)-one, 2-[(2S)-3amino-2-hydroxypropyl] hexacosahydro-3-methoxy-26-methyl-20,27-bis (methylene)-, (2R,3R,3aS,7R,8aS,9S,10aR,11S,12R,13aR,13bS,15S,18S,21S,24S,26R,28R,29aS)-, methane sulfonate (salt). It has a molecular weight of 826.0 (729.9 for free base). The empirical formula is $C_{40}H_{59}NO_{11} \cdot CH_4O_3S$. Eribulin mesylate has the following structure:

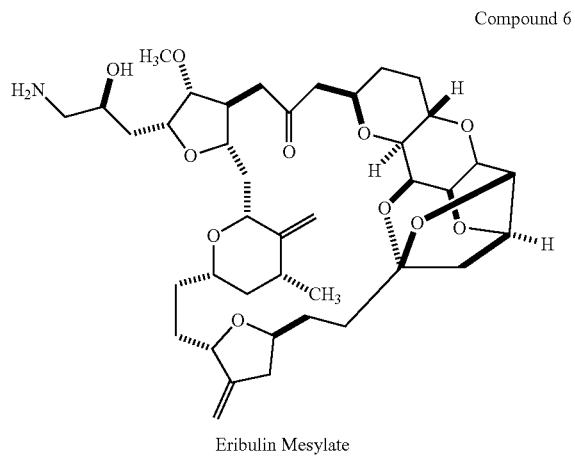

Compound 6

Eribulin Mesylate

Eribulin mesylate is marketed under trade name Halaven® by Eisai Inc. Halaven® is a clear, colorless, sterile solution for intravenous administration. Each vial contains 1 mg of eribulin mesylate as a 0.5 mg/mL solution in ethanol:water (5:95).

Methods for the synthesis of eribulin and other halichondrin B analogs are described in International Publication Nos. WO 2005118565, WO 2009046308, WO 2009064029, and WO 2009124237; U.S. Pat. No. 6,214,865; Austad et al., Synlett 24(3):333-337, 2013; Austad et al., Synlett. 24(3):327-332, 2013; and Chase et al, Synlett 24(3):323-326, 2013, each of which is incorporated herein by reference.

Generally, reproducibility and high purity levels are requirements for the preparation of anti-cancer agents at a commercial scale. However, prior processes for the preparation eribulin mesylate suffer serious drawbacks, including complex production processes that increase production time, typically resulting in lower than desired yields and/or purities. The loss of yield is believed to be due to the formation of unwanted isomer in the production process.

There is therefore a need for improved processes for the preparation of halichondrin B analogs, in particular eribulin mesylate intermediate of compound 2, that are amenable for manufacturing on a commercial scale, preferably with higher yields and/or purities than prior processes.

SUMMARY

The present application generally provides methods for macrocyclization of intermediates in the synthesis of eribulin or a pharmaceutically acceptable salt thereof, such as eribulin mesylate. The present application also provides intermediates that can be employed in the macrocyclization reactions described herein.

U.S. Pat. No. 9,303,039, which is incorporated herein by reference, discusses the process for the synthesis of eribulin mesylate. This patent discusses treating compound 1 with a fluoride source (tetrabutylammonium fluoride (TBAF)) at equilibration with a conjugate acid of imidazole (e.g. Imidazole HCl), in tetrahydrofuran as a solvent, which was believed to result in the deprotection of TBS group followed by oxy-Michael reaction, which leads to the formation of eribulin mesylate intermediate. The addition of dimethyl acetamide (DMAc) as a co-solvent in reaction was believed to improve the selectivity at C12 carbon (18:1 vs 4:1), and also shorten the reaction time (1-2 days vs. 7-10 days). The overall yield of intermediate was purportedly increased with the addition of amide solvents and a mixture of acetonitrile and water.

U.S. Pat. No. 6,214,865 (the '865 patent), which is also incorporated herein by reference, discusses the production of analogs of halichondrin B using 6 eq. of TBAF (1 M in THF) and 3 eq. of Imidazole HCl with 4:1 selectivity at C12 carbon and almost 3-4 days reaction time. These prolonged reaction times, however, lead to the formation of undesired impurities as a result of the degradation of the compound. The reactions were also sluggish and there appears to be no consistency in product formation.

Thus, there is a need for new and improved processes where the yield of eribulin mesylate compound 2 will be significantly increased and better selectivity at C12 carbon, with significant reduction of reaction times to avoid the degradation of the product. The present application provides processes that achieve any one or more of these goals.

In at least one embodiment in the present application, in contrast to the '865 patent, 20 eq. of TBAF (1 M in THF) and 10 eq. of Imidazole HCl were used, which generally resulted in better selectivity at C12 carbon. Additionally, increased overall yields were observed by maintaining anhydrous conditions using, e.g., molecular sieves and sodium sulphate, followed by lowering the temperature for sufficient time for maintaining reaction.

The present application provides an improved process as compared to the '865 patent that produces desired yields and quality with respect to eribulin mesylate compound 2. Eribulin mesylate compound 2 may then be used for the synthesis of eribulin mesylate. The resulting high quality and increased yield intermediate was achieved which also improves the overall yield of eribulin mesylate.

The improved process for the synthesis of eribulin intermediate generally comprises the steps of: a) De-protecting the eribulin-enone (compound 1) in tetrahydrofuran by using TBAF solution (1.0 M in THF), buffered with imidazole HCl in the presence of molecular sieve and sodium sulphate to get an insitu mixture of eribulin-dione diastereomer at C12 carbon (compound 2). Then ketalization is performed of eribulin-dione insitu intermediate containing mixture of diastereomer at C12 carbon (compound 2) with PPTS in dichloromethane to yield eribulin-diol (compound 3). The schematic representation of this improved process is depicted in FIG. 1.

DETAILED DESCRIPTION

Important aspects in the preparation of eribulin mesylate are quality and end product production costs. Owing to regulatory requirements, high quality standards have to be met. Of interest in this context are purity and content of the active compound. Coupled to purity, it is in particular the spectrum of by-products which needs to be monitored. Minor components have to be toxicologically qualified and assessed. Accordingly, such components are listed in specifications and the maximum occurrence in the product is defined. Generally, the by-product spectrum and the presence of individual contaminants are kept as low as possible to achieve the desire result.

As discussed above, the '865 patent discusses a process which includes the treatment of compound 1 therein with a fluoride source (such as Tetra butyl ammonium fluoride) and conjugated acid of imidazole in the presence of tetrahydrofuran to give selectivity at C12 carbon of 4:1 (Desired vs Undesired Isomer, respectively), which unfortunately will negatively impact product yield and commercial affordability for industries. Thus, there is a need for a process that improves the yield and/or quality of such products. Increases in the quality and yield of the intermediate will also improve the overall yield of eribulin mesylate.

In a first embodiment, the present application provides a process for the preparation of eribulin-diol (compound 3). The process begin according to this embodiment by first de-protecting eribulin-enone (compound 1) in tetrahydrofuran using excess equivalent of TBAF solution and imidazole HCl in the presence of molecular sieve and sodium sulphate, at lower temperature, to get an in situ mixture of eribulin-dione diastereomer at C12 carbon (compound 2). Subsequently, ketalization is performed of the eribulin-dione insitu intermediate containing the mixture of diastereomer at C12 carbon (compound 2) with Pyridinium para toluene sulfonate (PPTS) in dichloromethane to afford eribulin-diol (compound 3).

Figure 1:
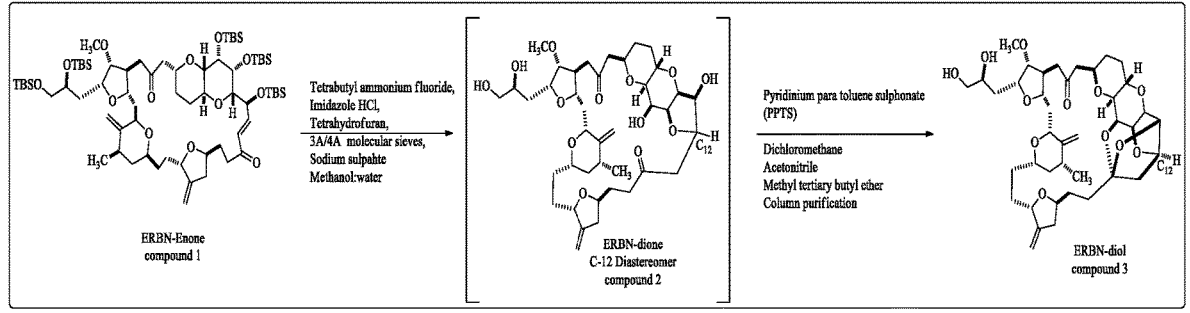
FIG. 1 depicts a schematic representation of a process for producing intermediate eribulin diol according to at least one embodiment of the processes disclosed herein.
Figure 2:
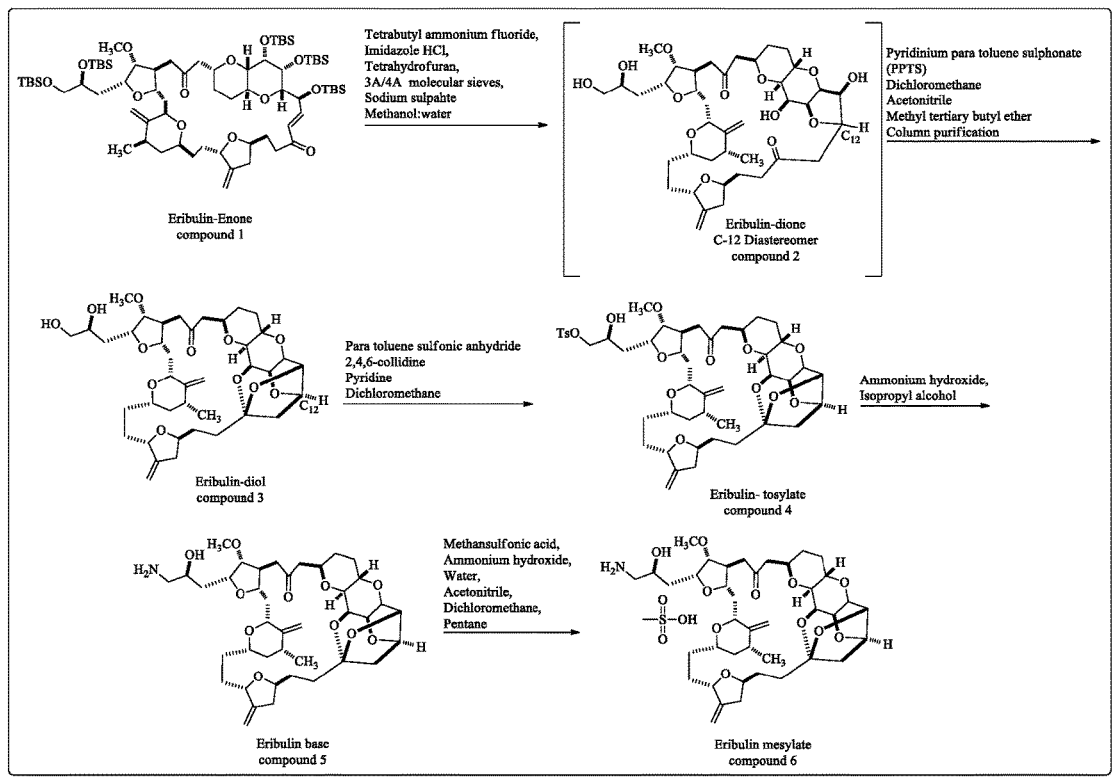
FIG. 2 depicts a schematic representation of a process for producing eribulin mesylate according to at least one embodiment of the processes disclosed herein.

In a second embodiment, the present application provides a process for the preparation of eribulin mesylate (compound 6) using a eribulin-diol (compound 3) intermediate, preferably produced as noted above. The steps of this embodiment include: tosylation reacting the eribulin-diol (compound 3) using para toluene sulfonic anhydride in presence of 2,4,6-collidine, using pyridine as base and dichloromethane as a solvent to get eribulin-tosylate (compound 4). The resulting eribulin-tosylate (compound 4) may then be amination reacted using ammonium hydroxide in isopropyl alcohol to get eribulin base (compound 5). Finally, eribulin mesylate (compound 6) is prepared by treating the eribulin base (compound 5) with methanesulfonic acid in an acetonitrile and water mixture. A schematic of this process is depicted in FIG. 2.

The presence of molecular sieves and sodium sulphate with excess equivalent of TBAF in solution and imidazole HCl, with lowering temperature in the process, improves the isolation of the desired isomer resulting in higher yield and better quality.

Certain specific aspects and embodiments of the present application will be explained in more detail with reference to the following examples, which are provided only for purposes of illustration and should not be construed as limiting the scope of the present application in any manner.

Experimental Section

Preparation of Eribulin-Diol (Compound 3)

Eribulin-enone (compound 1, 1 gm) was first dissolved in THF (30 ml) under argon atmosphere. The reaction mixture was then transferred into a mixture containing molecular sieves (2 gm) and sodium sulphate (2 gm) (preheated for 30 minutes at 110-120° C.). The reaction mass was then cooled to 0-5° C. Simultaneously, a solution containing Imidazole hydrochloride (0.7918 gm, 10 eq) in TBAF solution (1.0 M in THF) (15.23 ml, 20 eq.) was prepared. This solution was then charged in the above solution at 0-5° C. The reaction was then stirred for 24 hours at 10-20° C. The reaction was then filtered and distilled under vacuum to yield a residue. The residue was distilled with the addition of methanol:water (9:1) repeatedly to get a complete conversion with an improved yield of eribulin-dione (compound 2). The residue was dissolved in dichloromethane (50 ml) and charged with PPTS (0.9517 g) at 15-20° C. under argon atmosphere. The reaction was then stirred for 3 hours at 15-20° C. After completion of the reaction, pure eribulin-diol (compound 3) was obtained by column chromatography with the following characteristics: Yield: 0.3-0.4 g and Purity: 70%.

Preparation of Eribulin Base (Compound 5)

Eribulin-diol (compound 3, 1 gm) was dissolved in toluene (20 ml) and distilled under vacuum at a temperature below 40° C. to get eribulin-diol residue. This eribulin-diol was dissolved in dichloromethane (50 ml) to get a clear solution at room temperature. Preheated molecular sieves (2 gm) (at 110-120° C.) were charged in the above solution under argon atmosphere. Simultaneously, a solution was prepared of collidine (1.658 g), pyridine (50 mg) in DCM (100 ml). The solution in above reaction mixture was then charged at room temperature. The reaction mass was then cooled to −10 to −15° C. and a solution of Para toluene sulfonic anhydride (0.893 g) in DCM (50 ml) was added at a temperature below −10° C. Once the reaction was over, water (5 ml) was added. The solution was then filtered and washed with dichloromethane (10 ml) to get eribulin-tosylate.

Isopropyl alcohol (80 ml) and ammonium hydroxide (100 ml) was charged in eribulin-tosylate reaction mixture, and the reaction temperature between 25-30° C. was maintained for 48-72 hrs. Once the reaction was over, pure eribulin base (compound 5) was obtained by column chromatography. Further purification using preparative HPLC gives the desired quality product: Yield: 0.6-0.8 gm and Purity: 99%

Preparation of Eribulin Mesylate (Compound 6)

Eribulin base (1 g) was dissolved in acetonitrile (15.0 ml) & water (0.66 ml) at 25-30° C. to get a clear solution.

Methanesulfonic acid solution (0.129 gm in 4 ml NH4OH and 15 acetonitrile) was charged and stirred for 10 minutes. Once the reaction is over, the reaction mass is distilled to get a crude material. The crude material was dissolved in a solvent mixture of dichloromethane and n-pentane (25 ml) to get pure eribulin mesylate with the following characteristics: Yield: 0.8-0.9 gm and Purity: 98.5%

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A process for producing eribulin-diol consisting of:
de-protecting eribulin-enone (compound 1) using 20 eq. of a TBAF solution,
buffering the deprotected eribulin-enone (compound 1) using 10 eq. imidazole HCl in the presence of a mixture of anhydrous molecular sieves and sodium sulphate which is preheated at 110-120° C. for at least 30 minutes,
further cooling the de-protected eribulin-enone (compound 1) to 0-5° C.,
charging the cooled de-protected eribulin-enone (compound 1) with a solution containing imidazole hydrochloride in the TBAF solution and stirring for 24 hours between 10-20° C.,
further filtering and distilling the residue with the addition of methanol and water in the ratio of about 9:1 therewith producing an in situ mixture of eribulin-dione diastereomer at C12 carbon (compound 2); and
performing ketalization of the in situ mixture of eribulin-dione diastereomer at C12 carbon, therewith producing 70% pure eribulin-diol (compound 3).

\* \* \* \* \*